United States Patent [19]

Zook

[11] Patent Number: 5,330,452

[45] Date of Patent: * Jul. 19, 1994

[54] TOPICAL MEDICATING DEVICE

[76] Inventor: Gerald P. Zook, 909 N. 8th St., Apt. B-2, Tacoma, Wash. 98403

[*] Notice: The portion of the term of this patent subsequent to Jan. 26, 2010 has been disclaimed.

[21] Appl. No.: 69,411

[22] Filed: Jun. 1, 1993

[51] Int. Cl.$^5$ .............................................. A61F 13/02
[52] U.S. Cl. ................................. 604/307; 602/48; 602/42; 424/447
[58] Field of Search .................. 604/304, 307, 890.1, 604/892.1; 602/48, 51, 42, 41, 57, 58, 59; 424/447, 449

[56] References Cited

U.S. PATENT DOCUMENTS

| | | | |
|---|---|---|---|
| 3,419,006 | 12/1968 | King . | |
| 3,814,095 | 6/1974 | Lubens | 128/260 |
| 4,158,359 | 6/1979 | Kurokawa et al. | 128/630 |
| 4,379,454 | 4/1983 | Campbell et al. | 604/897 |
| 4,631,227 | 12/1986 | Nakamura | 428/283 |
| 4,788,971 | 12/1988 | Quisno | 128/743 |
| 4,842,931 | 6/1989 | Zook | 428/354 |
| 4,909,244 | 3/1990 | Quarfoot et al. | 602/48 |
| 4,988,341 | 1/1991 | Columbus et al. | 604/306 |
| 4,991,574 | 2/1991 | Pocknell | 128/156 |
| 5,015,228 | 5/1991 | Columbus et al. | 604/51 |
| 5,098,421 | 3/1992 | Zook | 604/367 |
| 5,106,629 | 4/1992 | Cartmell et al. | 424/445 |
| 5,167,649 | 12/1992 | Zook | 604/307 |
| 5,181,914 | 1/1993 | Zook | 604/307 |
| 5,204,110 | 4/1993 | Cartmell et al. | 602/57 |

*Primary Examiner*—Randall L. Green
*Assistant Examiner*—Paul Prebilic
*Attorney, Agent, or Firm*—John F. Ingman

[57] ABSTRACT

A topical medicating device includes a transparent viscoelastic gel pad having one or more pharmacologically-active substances incorporated therein; a sheet of transparent, impermeable, and elastic material providing an occlusive layer adjacent to the upper surface of the viscoelastic gel pad; an elastic retaining ring perimetrically surrounding the viscoelastic gel pad to prevent migration due to external pressure; and a porous meshwork attached to the elastic retaining ring so as to additionally anchor the gel pad from migration. The porous meshwork member may be located at the surface of the viscoelastic gel pad opposite the aforementioned occlusive covering sheet, or may run through the viscoelastic gel pad in its anchoring function. The viscoelastic gel pad, occlusive covering sheet, and retaining ring with porous meshwork may be affixed to a target skin surface of the patient by an adhesive tape bandage with a visual access opening. The adhesive bandage may be formed to integrally include the impermeable occlusive layer adjacent to the surface of the viscoelastic gel pad. As a topical anesthetic device, the liquid fraction of the viscoelastic gel pad may be a solution of alcohol and water, preferably, but not limited to, 70% ethyl alcohol, wherein is dissolved 10% to 40%, by weight, of Lidocaine, U.S.P./N.F.

19 Claims, 2 Drawing Sheets

TOPICAL MEDICATING DEVICE

BACKGROUND OF THE INVENTION

1. Field of the Invention

This invention relates to the general field of topical medicating devices and, more particularly, a topical anesthetic device utilizing a viscoelastic gel pad, supported by a perimetric elastic retaining ring and a porous meshwork attached to the elastic retaining ring, which is perfused with a topical anesthetic dissolved in the liquid fraction of the viscoelastic gel pad.

2. Description of the Prior Art

The inventor previously has developed a Medicating Device for Nails and Adjacent Tissue which utilizes a viscoelastic gel pad supported by a perimetric retaining ring and a porous meshwork attached to the ring, for which U.S. Pat. No. 5,181,914 was issued. In conjunction with the further development of pharmacological applications of the invention, it was discovered that the inventive structure of the Medicating Device for Nails and Adjacent Tissue has additional medicating applications beyond application to a digit, and is particularly valuable in use as a topical anesthetic device in conjunction with a local anesthetic, or a eutectic mixture of local anesthetics, which is compatible with the liquid fraction of the viscoelastic gel.

SUMMARY OF THE INVENTION

The invention, in the preferred embodiment, includes a transparent viscoelastic gel pad having one or more pharmacologically-active substances incorporated therein; a sheet of transparent, impermeable, and elastic material providing an occlusive layer adjacent to the upper surface of the viscoelastic gel pad; an elastic retaining ring perimetrically surrounding the viscoelastic gel pad to prevent migration due to external pressure; and a porous meshwork attached to the elastic retaining ring so as to additionally anchor the gel pad from migration. The porous meshwork member may be located at the surface of the viscoelastic gel pad opposite the aforementioned occlusive covering sheet, or may run through the viscoelastic gel pad in its anchoring function.

Affixing means are provided to secure the viscoelastic gel pad, occlusive covering sheet, and retaining ring with porous meshwork to the target skin surface of the patient, with a preferred affixing means including an adhesive tape bandage with a visual access opening. Alternatively, the adhesive bandage may be formed to integrally include the impermeable occlusive layer adjacent to the surface of the viscoelastic gel pad.

For use as a topical anesthetic device, the liquid fraction of the viscoelastic gel pad may be a solution of alcohol and water, preferably, but not limited to, 70% ethyl alcohol, wherein is dissolved 10% to 40%, by weight, of Lidocaine, U.S.P./N.F.. Alternatively, the liquid fraction of the viscoelastic gel may be a mineral oil, a silicone oil, an alcohol, or simply water. Other desirable anesthetic agents include, but are not limited to, a eutectic mixture of lidocaine and prilocaine, prilocaine, procains, tetracains, benzocaine, dibucaine, pramoxine, dyclonine, or cocaine. These anesthetic agents can be either in the free base form or salt form, such as the hydrochloride salt, whichever provides optimal drug delivery for a given viscelastic gel.

DETAILED DESCRIPTION OF THE INVENTION

Figure 1:
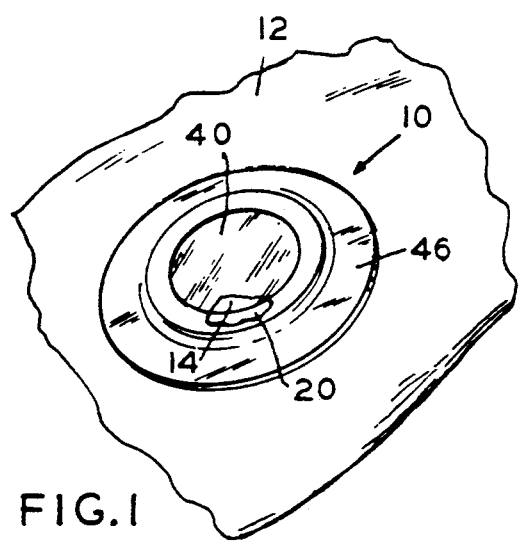
FIG. 1 illustrates a perspective view of the topical medicating device, as applied to a target skin surface of a patient.
Figure 2:
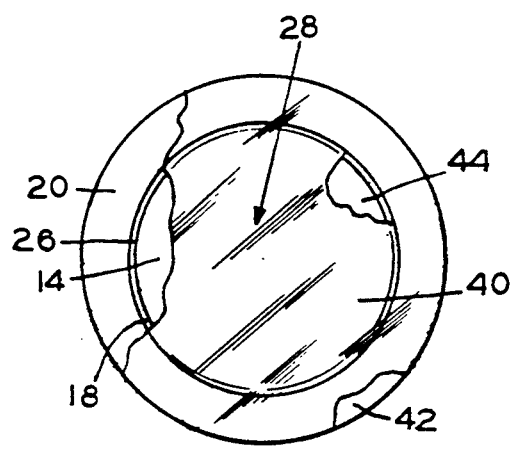
FIG. 2 illustrates a top plan view of the topical medicating device.

Turning now to the drawings, there is shown in FIG. 1 the topical medicating device 10 as applied to a target skin surface 12 of a patient.

In the preferred embodiment, a viscoelastic gel pad 14, formed preferably, but not necessarily, in a circular shape, is closely surrounded about its lateral perimeter 18 by a flexible retaining ring 20. The retaining ring 20 functions, in conjunction with a porous meshwork 22 discussed subsequently, to prevent migration of the viscoelastic gel pad 14 in response to externally applied pressures. The retaining ring 20 preferably is elastic and formed in the shape of the viscoelastic gel pad 14, and may be constructed of a soft compressible material such as foam rubber or a noncompressible material such as a silicone compound. A retaining ring 20 made of a soft material will not inflict pain on the target skin surface 12 of the patient when external force or pressure is applied. It is also desirable to use a material for the retaining ring 20 which is impervious to the liquid fraction of the viscoelastic gel pad 14 in order to prevent evaporation or bleeding of the liquid fraction and subsequent desiccation of the viscoelastic gel pad 14. When a porous material such as foam rubber is used, it is desirable to coat the inside perimetric surface 24 adjacent to the viscoelastic gel pad 14 with a thin layer of impermeable material 26, such as silicone rubber or the like, to prevent desiccation.

The viscoelastic gel pad 14 may utilize a gel having a alcohol, water, or oleaginous liquid fraction, or, a compatible combination thereof, such an alcohol and water liquid fraction, as discussed subsequently. A suitable viscoelastic gel pad 14 has been successfully formed by use of the hydrophilic gel described by King in U.S. Pat. No. 3,419,006. This viscoelastic gel pad 14 is highly flexible, conforming to the shape of the target skin surface 12 which is being anesthized or otherwise medicated, so as to apply the medication in a prescribed and even manner.

Figure 3:
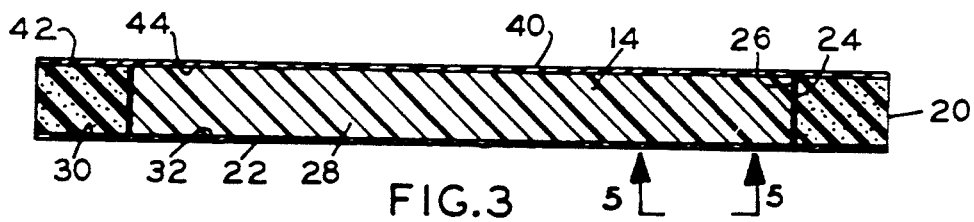
FIG. 3 illustrates a cross sectional view of the topical medicating device, wherein the porous meshwork attached to the perimetric retaining ring is fixed adjacent the viscoelastic gel pad.
Figure 4:
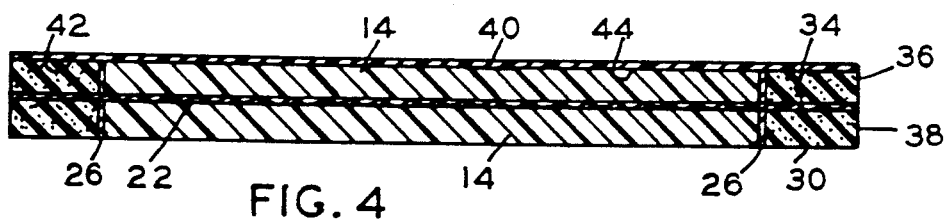
FIG. 4 illustrates a cross sectional view of an alternative configuration of the topical medicating device wherein the porous meshwork attached to the perimetric retaining ring passes through the viscoelastic gel pad.
Figure 5:
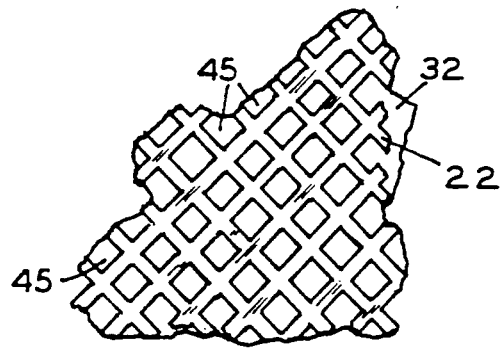
FIG. 5 illustrates the porous meshwork, as seen at line 5—5 of FIG. 3, supporting the lower surface of the viscoelastic gel pad.

However, the additional use of a porous meshwork 22 has been found to be desirable to provide additional structural integrity in keeping the viscoelastic gel pad 14 intact and preventing the pad 14 from being squeezed out of the retaining ring 20 when external pressures occur. Thus a porous meshwork 22 is affixed to the retaining ring 20 and extends across the central area 28 of the retaining ring 20 so as to support the viscoelastic gel pad 14 within the central area 28. The porous meshwork 22 may be formed of plastic, such as polyvinyl chloride, or an elastic material such as rubber which facilitates the stretching of the viscoelastic gel pad 14 in conforming to the contour of the target skin surface 12. As seen in FIG. 3, the porous meshwork 22 may be attached, as by adhesive at the lower surface 30 of the retaining ring 20, to extend across the central area 28 adjacent to the lower surface 32 of the viscoelastic gel pad 14. Such a porous meshwork 22 is desirably thin, so as not to provide an impediment to the direct contact of a medicated viscoelastic gel pad 14 against the target skin surface 12 of the patient. Alternatively, and generally preferable, the porous meshwork 22 may be affixed to extend from the inside perimetric surface 24 of the retaining ring 20 and thus pass within and through the viscoelastic gel pad 14 itself, providing support to the gel pad 14 without the porous meshwork 22 contacting the patient. Such affixation may occur by the attachment of the porous meshwork 22 within a split 34 within the retaining ring 20, or by joining two sections 36, 38 of a laterally split retaining ring 20 together with said porous meshwork 22 placed therebetween. FIGS. 3 and 5 illustrate a porous meshwork 22 extending beneath the viscoelastic gel pad 14, while FIG. 4 shows the porous meshwork 22 extending through the pad 14.

In order to prevent desiccation of the medicated viscoelastic gel pad 14, an impermeable sheet member 40 is attached, as by adhesive, about the upper surface 42 of the retaining ring 20. The sheet member 40, which preferably is elastic, provides an occlusive layer adjacent to the upper surface 44 of the viscoelastic gel pad 14 which prevents evaporation from the upper surface 44 and additionally helps hold the gel pad 14 within the retaining ring 20. The preferred impermeable sheet member 40 is transparent, which, with a transparent viscoelastic gel pad 14, allows the physician and the patient to observe the target skin surface 12 to which the topical medicating device 10 is applied, both initially and in subsequent monitoring. The porous meshwork 22 may also be transparent, although this is not necessary since the openings 45 in the porous meshwork 22 should be sufficient to allow observation.

The above described viscoelastic gel pad 14 is simple to utilize, wherein, for example, if a hydrophilic gel has been initially hydrated, the water may be evaporated off, and then the desiccated pad 14 soaked in the desired aqueous and/or alcoholic solution to reconstitute the pad with a medication incorporated therein.

Many medicinal agents or their salts can be incorporated into the present topical medicating device. For example antifungal agents such as ciclopirox, chloroxylenol, triacetin, sulconazole, nystatin, undecylenic acid, tolnaftate, miconizole, clotrimazole, oxiconazole, griseofulvin, econazole, ketoconazole, and amphotericin B may be incorporated into the gel. Antibiotic agents such as mupirocin, erythromycin, clindamycin, gentimycin, neomycin, polymyxin, bacitracin, silver sulfadiazine, and the like may also be incorporated into the gel. Antiseptic agents such as iodine, povidone-iodine, benzalkonium chloride, benzoic acid, chlorhexidine, nitrofurazone, benzoyl peroxide, hydrogen peroxide, hexachlorophene, phenol, resorcinol, and cetylpyridinium chloride likewise could be incorporated into the present invention. Furthermore, anti-inflammatories such as hydrocortisone, prednisone, triamcilolone, betamethasone, dexamethasone, and the like may be incorporated into the gel. Still further, local aesthetics such as benzocaine, lidocaine, as specifically discussed below, procaine, bupivicaine, a eutectic mixture of prilocaine and lidocaine, phenol, or the like may also be incorporated into the gel. Additional agents that could be incorporated include penetration enhancers such as dimethyl sulfoxide or octolyphenylpolyethelene glycol, keratolytic agents such as salicylic acid, enzymes such as proteases and nucleases, hormones such as insulin, vesicants such as cantharadin, caustics such as podophyllin, plant and animal venom denaturants such as aluminum sulfate, substance P depleters such as capsaicin, and a myriad of additional pharmacologically active substances.

Of particular value is a unique formulation, whereby lidocaine-base, in the form of Lidocaine U.S.P./N.F., may be dissolved in an alcohol and water solution where the alcohol portion of the alcohol and water solution dissolves the lidocaine-base (not dissolvable in water) while the water portion provides for optimum absorption and retention in a hydrophilic gel. While various alcohol and water solutions provide acceptable results, a 70% ethyl alcohol solution is preferred with Lidocaine U.S.P./N.F. dissolved therein in an amount within the range of 10% to 40%, by weight. Such use of the lidocaine-base is novel, previous anesthetic application utilizing lidocaine hydrochloride, which is freely soluble in water but apparently too polar to pass through the epidermis, requiring an injection via needle and syringe, or a high pressure jet-injection device.

Indeed, it may be highly advantageous, such as with a topical anesthetic device 10, to instruct the patient to apply the device 10 to a target skin surface 12 location preliminary to arrival at the physician's office or clinic. Thus, rather than having to wait a considerable period for alternative topically applied anesthesia to deaden the target skin surface 12, the patient is immediately available for surgery or other treatment.

The ability of a patient to apply the topical medicating device 10, and particularly as a topical anesthetic device, is enhanced by the transparent nature of the viscoelastic gel pad 14 and occlusive covering sheet member 40. Indeed, the physician may place a mark upon the target skin surface 12 location providing the patient with an identifiable "target" which is observable through the device 10.

Figure 6:
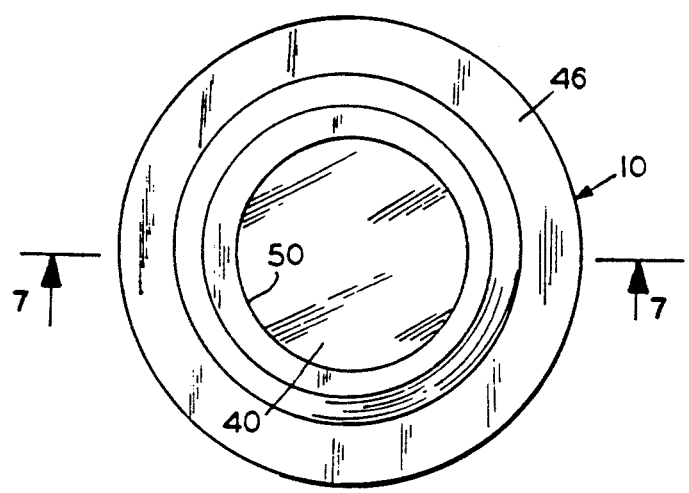
FIG. 6 illustrates a top plan view of the topical medicating device affixed to an adhesive bandage.
Figure 7:
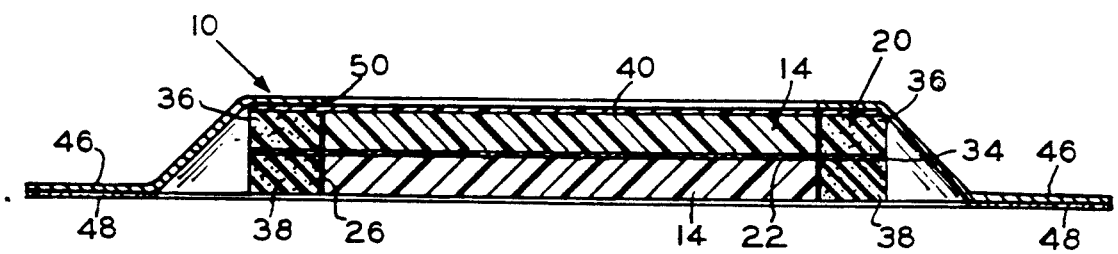
FIG. 7 illustrates a cross sectional view of the topical medicating device of FIG. 6 with adhesive bandage.
Figure 8:
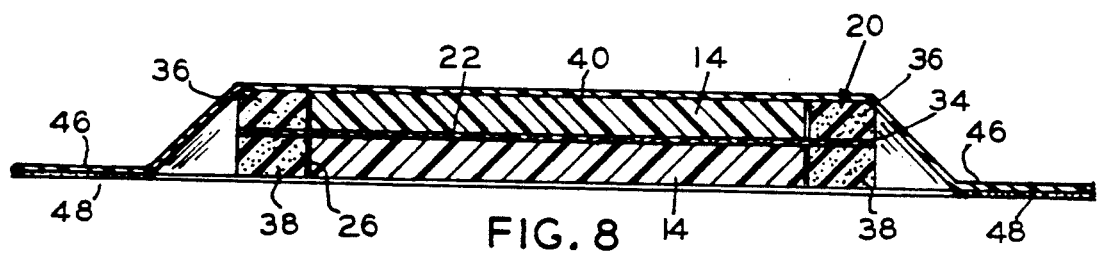
FIG. 8 illustrates a cross sectional view of the topical medicating device where the adhesive bandage integrally includes an impermeable sheet member atop the retaining ring of the device.

A means for applying the viscoelastic gel pad 14 and retaining ring 20 is by the use of an adhesive bandage 46 where a layer of pressure sensitive adhesive 48 holds the device 10 against the target skin surface 12. As illustrated in FIGS. 6 and 7, such an adhesive bandage 46 preferably includes an opening or window 50 through which observation may occur. The bandage 46 may be attached at the upper surface 42 of the retaining ring 20, along with the sheet member 40. Alternatively, the adhesive bandage 46 may be formed to integrally include the impermeable sheet member 40, wherein the adhesive bandage 46 be formed of transparent material, as shown in FIG. 8. The adhesive bandage 46 preferably is waterproof to permit bathing without disrupting the medicating device 10.

It is thought that the topical medicating device 10, including its use as a topical anesthetic device with lidocaine-base dissolved in a alcohol and water solution as the liquid fraction of the viscoelastic gel pad, of the present invention and its many attendant advantages will be understood from the foregoing description and that it will be apparent that various changes in form, construction and arrangement of the parts thereof may be made without departing from the spirit and scope of the invention or sacrificing all of its material advantages, the form hereinbefore described being merely an exemplary embodiment thereof.

I claim:

1. A topical medicating device, comprising:
   a. a viscoelastic gel pad, having an upper surface, a lower surface, and a lateral perimeter;
   b. a flexible retaining ring formed to fit closely about the lateral perimeter of said viscoelastic gel pad; said retaining ring having an upper surface and a lower surface, and bounding a central area wherein said viscoelastic gel pad is located;
   c. an impermeable sheet member, attached about the upper surface of said retaining ring, which provides an occlusive layer adjacent to said upper surface of said viscoelastic gel pad;
   d. a thin, porous meshwork affixed to said retaining ring and extending across said central area of said retaining ring to support said viscoelastic gel pad within said central area; and
   e. means for attaching said viscoelastic gel pad and said flexible retaining ring with affixed porous meshwork to a target skin surface upon a patient.

2. The topical medicating device, as recited in claim 1, wherein said thin porous meshwork is positioned adjacent to said lower surface of said viscoelastic gel pad.

3. The topical medicating device, as recited in claim 1, wherein said thin, porous meshwork is positioned within and extends through said viscoelastic gel pad.

4. The topical medicating device, as recited in claim 1, wherein said means for attaching said topical medicating device to a patient includes an adhesive bandage.

5. The topical medicating device, as recited in claim 4, wherein said adhesive bandage includes a window adjacent said impermeable sheet member.

6. The topical medicating device, as recited in claim 4, wherein said adhesive bandage is formed to integrally include said impermeable sheet member.

7. The topical medicating device, as recited in claim 1, wherein said viscoelastic gel pad and impermeable, elastic sheet member are transparent.

8. The topical medicating device, as recited in claim 1, wherein said viscoelastic gel pad is perfused with one or more pharmacologically active agents.

9. A topical anesthetic device, comprising:
   a. a viscoelastic gel pad, having an upper surface, a lower surface, and a lateral perimeter, said viscoelastic gel pad being perfused with an anesthetic;
   b. a flexible retaining ring formed to fit closely about the lateral perimeter of said viscoelastic gel pad; said retaining ring having an upper surface and a lower surface, and bounding a central area wherein said viscoelastic gel pad is located;
   c. an impermeable sheet member, attached about the upper surface of said retaining ring, which provides an occlusive layer adjacent to said upper surface of said viscoelastic gel pad;
   d. a thin, porous meshwork affixed to said retaining ring and extending across said central area of said retaining ring to support said viscoelastic gel pad within said central area; and
   e. means for attaching said viscoelastic gel pad and said flexible retaining ring with affixed porous meshwork to a target skin surface upon a patient.

10. The topical anesthetic device, as recited in claim 9, wherein said thin porous meshwork is positioned adjacent to said lower surface of said viscoelastic gel pad.

11. The topical anesthetic device, as recited in claim 9, wherein said thin, porous meshwork is positioned within and extends through said viscoelastic gel pad.

12. The topical anesthetic device, as recited in claim 9, wherein said means for attaching said topical medicating device to a patient includes an adhesive bandage.

13. The topical anesthetic device, as recited in claim 12, wherein said adhesive bandage includes a window adjacent said impermeable elastic sheet member.

14. The topical anesthetic device, as recited in claim 12, wherein said adhesive bandage is formed to integrally include said impermeable sheet member.

15. The topical anesthetic device, as recited in claim 9, wherein said viscoelastic gel pad and said impermeable sheet member are transparent.

16. The topical anesthetic device, as recited in claim 9, said viscoelastic gel pad having a liquid fraction, said liquid fraction is a solution of alcohol and water in which the anesthetic lidocaine, U.S.P./N.F. is dissolved.

17. The topical anesthetic device, as recited in claim 16, wherein said liquid fraction of said viscoelastic gel pad is approximately 70% ethyl alcohol, by weight.

18. The topical anesthetic device, as recited in claim 16, wherein said liquid fraction of said viscoelastic gel includes between 10 percent and 40 percent, by weight, of lidocaine, U.S.P./N.F. dissolved therein.

19. The topical medicating device, as recited in claim 8, wherein said pharmacologically active agents are antifungal agents, antibiotic agents, antiseptic agents, anti-inflammatories, local anesthetics, penetration enhancers, keratolytic agents, enzymes, hormones, vesicants, caustics, plant and animal venom denaturants, or substance P depleters.

* * * * *